US010493146B2

(12) United States Patent
Zeng et al.

(10) Patent No.: US 10,493,146 B2
(45) Date of Patent: Dec. 3, 2019

(54) LIVE ATTENUATED VIRAL VACCINE CREATED BY SELF-ATTENUATION WITH SPECIES-SPECIFIC ARTIFICIAL MICRORNA

(71) Applicant: Texas Tech University System, Lubbock, TX (US)

(72) Inventors: Mingtao Zeng, El Paso, TX (US); Junwei Li, El Paso, TX (US)

(73) Assignee: Texas Tech University System, Lubbock, TX (US)

( * ) Notice: Subject to any disclaimer, the term of this patent is extended or adjusted under 35 U.S.C. 154(b) by 0 days.

(21) Appl. No.: 15/518,781

(22) PCT Filed: Oct. 14, 2015

(86) PCT No.: PCT/US2015/055495
§ 371 (c)(1),
(2) Date: Apr. 13, 2017

(87) PCT Pub. No.: WO2016/061200
PCT Pub. Date: Apr. 21, 2016

(65) Prior Publication Data
US 2017/0232097 A1   Aug. 17, 2017

Related U.S. Application Data

(60) Provisional application No. 62/063,765, filed on Oct. 14, 2014.

(51) Int. Cl.
| | |
|---|---|
| *A61K 39/145* | (2006.01) |
| *C12N 15/113* | (2010.01) |
| *C12N 7/00* | (2006.01) |
| *A61K 39/12* | (2006.01) |
| *C12N 15/86* | (2006.01) |
| *A61K 39/00* | (2006.01) |

(52) U.S. Cl.
CPC ............ *A61K 39/145* (2013.01); *A61K 39/12* (2013.01); *C12N 7/00* (2013.01); *C12N 15/1131* (2013.01); *C12N 15/86* (2013.01); *A61K 2039/53* (2013.01); *A61K 2039/545* (2013.01); *A61K 2039/55* (2013.01); *A61K 2039/575* (2013.01); *C12N 2310/141* (2013.01); *C12N 2330/51* (2013.01); *C12N 2760/16123* (2013.01); *C12N 2760/16134* (2013.01); *C12N 2760/16151* (2013.01); *C12N 2760/16161* (2013.01); *C12N 2760/16171* (2013.01)

(58) Field of Classification Search
None
See application file for complete search history.

(56) References Cited

U.S. PATENT DOCUMENTS

2012/0148622 A1*  6/2012  tenOever .......... A61K 39/145
                                                    424/209.1

OTHER PUBLICATIONS

Umbach et al. (Nature, 2008, vol. 454, p. 780-785).*
Schmid et al. (Journal of Virology, Dec. 2013, p. 2333-2336).*
Zhang et al. (Virology Journal, Feb. 2012, p. 1-11).*
Barnes D, et al. (Sep. 11, 2008) Harnessing endogenous miRNAs to control virus tissue tropism as a strategy for developing attenuated virus vaccines. Cell host & microbe 4(3):239-248.
Berezikov E, et al. (Dec. 2006) Diversity of microRNAs in human and chimpanzee brain. Nature genetics 38 (12):1375-1377.
Boden D, et al. (2004) Enhanced gene silencing of HIV-1 specific siRNA using microRNA designed hairpins. Nucleic acids research 32(3):1154-1158.
Chen SC, et al. (Jul. 18, 2011) Expression of multiple artificial microRNAs from a chicken miRNA126-based lentiviral vector. PloS one 6(7):e22437.
Edge RE, et al. (Aug. 2008) A let-7 MicroRNA-sensitive vesicular stomatitis virus demonstrates tumor-specific replication. Molecular therapy : the journal of the American Society of Gene Therapy 16(8):1437-1443.
Hoffmann E, et al. (May 23, 2000) A DNA transfection system for generation of influenza A virus from eight plasmids. Proceedings of the National Academy of Sciences of the United States of America 97(11):6108-6113.
International Search Report PCT/US2015/055495 [KIPO] dated Feb. 29, 2016.
Kelly EJ, et al. (Nov. 2008) Engineering microRNA responsiveness to decrease virus pathogenicity. Nature medicine 14(11):1278-1283.
Kumar M, et al. (2012) Control of HBV replication by antiviral microRNAs transferred by lentiviral vectors for potential cell and gene therapy approaches. Antiviral therapy 17(3):519-528.
Lee TC, et al. (2010) Utilizing liver-specific microRNA-122 to modulate replication of dengue virus replicon. Biochemical and biophysical research communications 396(3):596-601.
Li J, et al. (May 2014) Intranasal immunization with influenza antigens conjugated with cholera toxin subunit B stimulates broad spectrum immunity against influenza viruses. Human vaccines & immunotherapeutics 10(6).
Manicassamy B, et al. (Jun. 22, 2010) Analysis of in vivo dynamics of influenza virus infection in mice using a GFP reporter virus. Proceedings of the National Academy of Sciences of the United States of America 107 (25):11531-11536.
Perez, J. T. et al., 'MicroRNA-mediated species-specific attenuation of influenza A virus', Nature Biotechnology, Jun. 2009, vol. 27, No. 6, pp. 572-576.
Pica N, et al. (Oct. 2012) NS1-truncated live attenuated virus vaccine provides robust protection to aged mice from viral challenge. Journal of virology 86(19):10293-10301.
Rouha H, et al. (2010) Functional microRNA generated from a cytoplasmic RNA virus. Nucleic acids research 38 (22):8328-8337.

(Continued)

*Primary Examiner* — Agnieszka Boesen
(74) *Attorney, Agent, or Firm* — Edwin S. Flores; Daniel J. Chalker; Chalker Flores, LLP

(57) ABSTRACT

The present invention includes a live attenuated virus and methods of making the same comprising an isolated virus comprising a viral genome that expresses one or more viral antigens; and one or more exogenous species-specific microRNAs inserted into the viral genome and expressed thereby, wherein the species-specific microRNAs are ubiquitously expressed in a viral target species cell but not in a viral propagation cell.

13 Claims, 9 Drawing Sheets

Specification includes a Sequence Listing.

(56) References Cited

OTHER PUBLICATIONS

Rubinson DA, et al. (Mar. 2003) A lentivirus-based system to functionally silence genes in primary mammalian cells, stem cells and transgenic mice by RNA interference. Nature genetics 33(3):401-406.

Schmid, S. et al., 'A versatile RNA vector for delivery of coding and noncoding RNAs',Journal of Virology, Feb. 2014, vol. 88, No. 4, pp. 2333-2336.

Shapiro JS, et al. (2010) Noncanonical cytoplasmic processing of viral microRNAs. Rna 16(11):2068-2074.

TenOever, B. R., 'RNA viruses and the host microRNA machinery', Nature Reviews Microbiology, Mar. 2013, vol. 11, No. 3, pp. 169-180.

Varble A, et al. (Jun. 22, 2010) Engineered RNA viral synthesis of microRNAs. Proceedings of the National Academy of Sciences of the United States of America 107(25):11519-11524.

Vignuzzi M, et al. (Jan. 19, 2006) Quasispecies diversity determines pathogenesis through cooperative interactions in a viral population. Nature 439(7074):344-348.

Wu Z, et al. (Oct. 18, 2011) Broad-spectrum antiviral activity of RNA interference against four genotypes of Japanese encephalitis virus based on single microRNA polycistrons. PloS one 6(10):e26304.

Yang C, et al. (Jun. 4, 2013) Deliberate reduction of hemagglutinin and neuraminidase expression of influenza virus leads to an ultraprotective live vaccine in mice. Proceedings of the National Academy of Sciences of the United States of America 110(23):9481-9486.

Ylosmaki E, et al. (Jan. 2013) Attenuation of Semliki Forest virus neurovirulence by microRNA-mediated detargeting. Journal of virology 87(1):335-344.

Zhang R, et al. (2008) Molecular evolution of a primate-specific microRNA family. Molecular biology and evolution 25 (7):1493-1502.

Zhang T, et al. (2012) Efficient inhibition of HIV-1 replication by an artificial polycistronic miRNA construct. Virology journal 9:118.

Extended European Search Report EP15850461.3 dated May 28, 2018.

Ge et al: "RNA interference of influenza virus production by directly targeting mRNA for degradation and indirectly inhibiting all viral RNA transcription", Proceedings of the National Academy of Sciences—National Academy of Sciences, us, vol. 100, No. 5, Mar. 4, 2003 (Mar. 4, 2003), pp. 2718-2723.

Li et al: "Generation of a safe 1-15 and effective live viral vaccine by virus self-attenuation using species-specific artificial microRNA" Journal of Controlled Release,vol. 207, Apr. 7, 2015 (Apr. 7, 2015), pp. 70-76.

Zhou et al: "Effective small interfering RNAs targeting matrix and nucleocapsid protein gene inhibit influenza A virus replication in cells and mice", Antiviral Research, Elsevier BV, vol. 76, No. 2, Sep. 19, 2007(Sep. 19, 2007), pp. 186-193.

\* cited by examiner

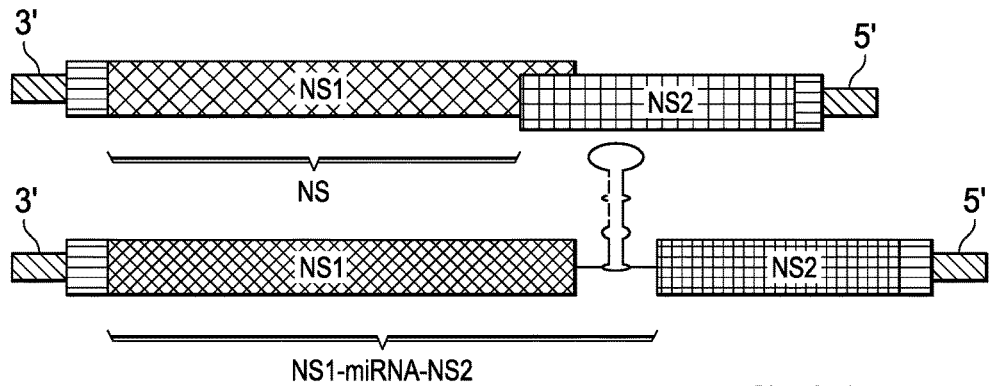

FIG. 2A

PRE-miR-93:
GTGCTACCGCACTGTGGGTACTTGCTGCTCCAGCAG
GGCACGCACAGCGTCCGTGGAGGGAAAGGCCTTTTC
CCCACTTCTTAACCTTCACTGAGAGGGTGGTTGGGGT
CTGTTTCACTCCATGTGTCCTAGATCCTGTGCTACAGA
CCTTCCTTTCTGTCCTCCCGTCTTGGACCTCAGTCCT
GGGGGCTCCAAA*GTGCTGTTCGTGCAGGTAG*TGTGA
TTACCCAACCT*ACTGCTGAGCTAGCACTTC*CCGAGCC
CCCGGGACACGTTCTCTCTGCCAATTGTCTTCTTGGC
TGAGCTCCCCAAGCTCCATCTGTCATGCTGGGGAGC
CCAGTGGCGTTCAAAAGGGTCTGGTCTCCCTCACAG
GACAGCTGAACTCCGGGACTGGCCAGTGTTGAGAGG
CGGAGACTTGGGCAATTGCTGGACGCTGCCC

FIG. 2B

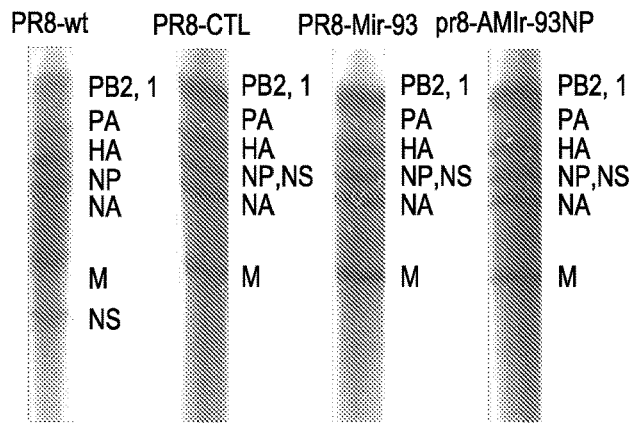

FIG. 2C

LIVE ATTENUATED VIRAL VACCINE CREATED BY SELF-ATTENUATION WITH SPECIES-SPECIFIC ARTIFICIAL MICRORNA

CROSS-REFERENCE TO RELATED APPLICATIONS

This application claims priority to, and is a National Stage Patent Application of International Application No. PCT/US2015/055495 filed on Oct. 14, 2015, which claims priority to U.S. Provisional Patent Application Ser. No. 62/063,765, filed on Oct. 14, 2014. The contents of both applications are incorporated by reference herein in their entirety.

TECHNICAL FIELD OF THE INVENTION

The present invention relates in general to the field of live attenuated vaccines, and more particularly, to novel vaccines that are self-attenuating by introducing species-specific artificial miRNAs.

INCORPORATION-BY-REFERENCE OF MATERIALS FILED ON COMPACT DISC

The present application includes a Sequence Listing which has been submitted in ASCII format via EFS-Web and is hereby incorporated by reference in its entirety. Said ASCII copy, created on Oct. 26, 2015, is named TECH1122US_SeqList.txt and is 2 KB in size.

BACKGROUND OF THE INVENTION

Without limiting the scope of the invention, its background is described in connection with influenza vaccines.

SUMMARY OF THE INVENTION

In one embodiment, the present invention includes a live attenuated virus comprising: an isolated virus comprising a viral genome that expresses one or more viral antigens; and one or more exogenous species-specific microRNAs inserted into the viral genome and expressed thereby, wherein the species-specific microRNAs are ubiquitously expressed in a viral target species cell but not in a viral propagation cell. In one aspect, the species-specific microRNA is a mature and functional artificial microRNA that specifically silences influenza Nucleoprotein (NP) gene expression. In another aspect, the microRNA is ubiquitously expressed in mammalian cells but not in avian cells. In another aspect, the microRNA is not expressed in avian cells. In another aspect, the microRNA comprises a miR-93 backbone-based cassette for species-specific microRNA expression. In another aspect, the virus expresses one or more viral antigens that confer protection against H1N1, pandemic H1N1, and H3N2. In another aspect, the virus is packaged into a vaccine. In another aspect, the virus is adapted for pulmonary, oral, nasal, or mucosal administration. In another aspect, the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens. In another aspect, the virus is packaged into a vaccine and less than 1,000, 500, 400, 300, 200, 100, 90, 80, 70, 60, 50, 40, 30, 20, 10 or 1 viral particle(s) confer protective immunity to the virus. In another aspect, the mature miR-93 loop is replaced with sequence within the mature miR-93 loop was replaced with the sequence: 5'-AGAUCUUAUAUC-UUCGGAGUGUGAUUACCCAACCUCUC-CGAAGAAAUAAGAUCC-3' (SEQ ID NO.:1). In another aspect, the virus has an $EID_{50}$ of 10 or less. In another aspect, the virus comprises multiple artificial miRNA expression cassettes. In another aspect, the virus comprises one or more artificial miRNA expression cassettes in the nonstructural (NS) gene segment.

In another embodiment, the present invention includes a method of making a virus comprising: obtaining an isolated virus comprising a viral genome that expresses one or more viral antigens; and inserting into the viral genome one or more exogenous species-specific microRNAs inserted into the viral genome and expressed thereby, wherein the species-specific microRNAs are ubiquitously expressed in a viral target species cell but not in a viral propagation cell. In one aspect, the species-specific microRNA is a mature and functional artificial microRNA that specifically silences influenza Nucleoprotein (NP) gene expression. In another aspect, the microRNA is ubiquitously expressed in mammalian cells but not in avian cells. In another aspect, the microRNA is not expressed in avian cells. In another aspect, the microRNA comprises a miR-93 backbone-based cassette for species-specific microRNA expression. In another aspect, the virus expresses one or more viral antigens that confer protection against H1N1, pandemic H1N1, and H3N2. In another aspect, the virus is packaged into a vaccine. In another aspect, the virus is adapted for pulmonary, oral, nasal, or mucosal administration. In another aspect, the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens. In another aspect, the virus is packaged into a vaccine and less than 1,000, 500, 400, 300, 200, 100, 90, 80, 70, 60, 50, 40, 30, 20, 10 or 1 viral particle(s) confer protective immunity to the virus. In another aspect, the mature miR-93 loop is replaced with sequence within the mature miR-93 loop was replaced with the sequence: 5'-AGAUCUUAUAUCUUCG-GAGUGUGAUUACCCAACCUCUC-CGAAGAAAUAAGAUCC-3' (SEQ ID NO.:1). In another aspect, the virus has an $EID_{50}$ of 10 or less. In another aspect, the virus comprises multiple artificial miRNA expression cassettes. In another aspect, the virus comprises one or more artificial miRNA expression cassettes in the nonstructural (NS) gene segment.

In yet another embodiment, the present invention includes a method of testing a virus for making a vaccine comprising: selecting a cell for propagation of a virus that does not express a specific miRNA; obtaining an isolated virus comprising a viral genome that expresses one or more viral antigens; inserting into the viral genome one or more exogenous species-specific microRNAs inserted into the viral genome and expressed thereby, wherein the species-specific microRNAs are ubiquitously expressed in a viral target species cell but not in a viral propagation cell; and determining if the virus propagates in the viral propagation cell but is attenuated in the viral target species cell.

BRIEF DESCRIPTION OF THE DRAWINGS

For a more complete understanding of the features and advantages of the present invention, reference is now made to the detailed description of the invention along with the accompanying figures and in which:

FIG. 1C is an evaluation of natural miR-93 expression in DF1, MDCK, MEF, and A549 cell lines. U6 was used as a control RNA probe. FIG. 1D is an evaluation of miR-93 expression in cells infected with influenza virus PR8. NP protein expression was used to verify viral infection, and β-actin was used as loading control.

FIGS. 2A and 2B show the engineering of NS gene segment and design of miR-93 expression cassette. FIG. 2A is a diagram of engineered and original NS gene segments. Green represents 5' and 3' noncoding regions; blue represents the packaging signal within the open reading frame; orange with blue to the left represents the NS1 coding sequence; yellow with blue to the right represent the NS2 coding sequence. (Top) Organization of the original NS gene segment. (Bottom) Organization of the modified NS gene segment engineered with ctl, miR-93, or amiR-93NP expression cassettes. FIG. 2B shows the sequence of the miR-93 locus inserted into the NS gene segment (SEQ ID NO: 2); red denotes the replacement sequence for expression of the artificial microRNA directed against NP.

FIGS. 2C to 2F show the verification of rescued influenza viruses and NP expression in wild-type and engineered PR8 viruses. FIG. 2C shows RNA that was isolated from purified PR8 wild type, PR8-ctl, PR8-miR-93, and PR8-amiR93-NP influenza viruses, and 1 μg was separated on a 4% acrylamide TBE urea gel. Bands were visualized by silver staining. Each RNA segment is labeled to the right of the gel. FIG. 2D shows that the NS and NP gene segments were amplified by RT-PCR and separated by electrophoresis on an agarose gel. FIG. 2E shows that A549 cells were infected with influenza virus (MOI=1), and samples were harvested at 8 hours post-infection. NP protein and amiRNA directed against the NP gene were analyzed by western blot and northern blot, respectively. FIG. 2F shows that MEF and MEF Dicer$^{-/-}$ cells were infected with different influenza viruses, then harvested at 8 and 16 hours post-infection. NP and NS1 proteins were analyzed by western blot.

FIG. 3A shows that the MDCK cell line was infected with PR8-wt or PR8-ctl virus. FIG. 3B shows that the MDCK cell line was infected with PR8-miR-93 or PR8-amiR-93NP virus.

FIG. 5A shows mouse weight change after challenge with wild type PR8 influenza virus and (FIG. 5B) survival rate (*p>0.05) are shown.

FIG. 5C shows the mouse weight change after $10^4$ PFU HK68 H3N2 influenza virus, and FIG. 5D shows the survival rate for mice challenged with HK68 H3N2 influenza virus. FIG. 5E shows the mouse weight change, and FIG. 5F the survival rate for mice challenged with CA09 H1N1 pandemic influenza virus (**p<0.05).

DETAILED DESCRIPTION OF THE INVENTION

Figure 1A:
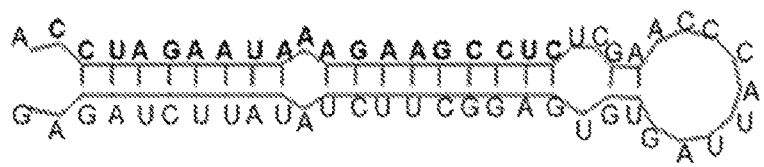
FIG. 1A shows the design of an artificial miRNA based on the miR-93 backbone. Sequence and secondary structure of amiR-93NP (SEQ ID NO.: 1). The mature artificial miR93-NP sequence is in bold.

While the making and using of various embodiments of the present invention are discussed in detail below, it should be appreciated that the present invention provides many applicable inventive concepts that can be embodied in a wide variety of specific contexts. The specific embodiments discussed herein are merely illustrative of specific ways to make and use the invention and do not delimit the scope of the invention.

To facilitate the understanding of this invention, a number of terms are defined below. Terms defined herein have meanings as commonly understood by a person of ordinary skill in the areas relevant to the present invention. Terms such as "a", "an" and "the" are not intended to refer to only a singular entity, but include the general class of which a specific example may be used for illustration. The terminology herein is used to describe specific embodiments of the invention, but their usage does not delimit the invention, except as outlined in the claims.

As used herein, the term "attenuated vaccine" refers to a virus or pathogen that has been modified to reduce its virulence while maintaining the virus or pathogen viable. The term "live attenuated vaccine" when referring to a virus described a virus that remains viable for infecting and replicating within a target host. The present invention can be used to modify a wide variety or viruses, e.g., adenovirus, measles, mumps, rubella, influenza, chicken pox, smallpox, polio, rotavirus, yellow fever, chikungunya, hantavirus, cytomegalovirus, dengue, Epstein-Barr virus, hepatitis A, B, C, or E, human papilloma virus, encephalitis, HIV and rabies, to name a few. Attenuated vaccines can be formulated for use in mammals, e.g., humans. Furthermore, the present invention can be designed, following the teachings herein, to be grown in an avian system for use as a vaccine in a mammalian, vice verse, of using other viral expression system (e.g., insect cells) for use in non-insects.

As used herein, the term "vaccine", "vaccination" and "vaccinating" refer to compositions and methods for modulating an immune response to a selected antigen such that the response is more efficient, more rapid, greater in magnitude, and/or more easily induced.

As used herein, the term "modulating an immune response" refers to the stimulation and/or activation of an immune response to a selected antigen, but it also refers to the suppression, elimination, or attenuation of an immune response to a selected antigen.

As used herein, the "antigen" refers to a molecule that can initiate a humoral and/or a cellular immune response in a recipient to the antigen. Antigens can be any type of biologic molecule including, for example, simple intermediatery metabolites, sugars, lipids, and hormones as well as macromolecules such as complex carbohydrates, phospholipids, nucleic acids and proteins. Common categories of antigens include, but are not limited to, viral antigens, bacterial antigens, fungal antigens, protozoa and other parasitic antigens, tumor antigens, antigens involved in autoimmune disease, allergy and graft rejection, and other miscellaneous antigens.

The compositions, vaccines or formulations of the invention can be used, for example, to modulate an immune response in a mammal such as a human.

Vaccination with live attenuated vaccines (LAVs) is an effective way for prevention of infectious disease. While several methods are employed to create them, efficacy and safety are still a challenge. The inventors demonstrate herein the design and manufacture of a self-attenuated RNA virus expressing a species-specific artificial microRNA. Using influenza virus as an example, the inventors designed and produced an attenuated virus carrying a mammalian-specific miR-93 expression cassette that expresses a viral nucleoprotein (NP)-specific artificial microRNA from an insertion site within the non-structural (NS) gene segment. The resulting engineered influenza virus, PR8-amiR-93NP, produced mature and functional artificial microRNA against NP in mammalian cells, but not in avian cells. Furthermore, PR8-amiR-93NP was attenuated by $10^4$ fold in mice compared with its wild-type counterpart. Importantly, intranasal immunization with PR8-amiR-93NP conferred cross-protective immunity against heterologous influenza virus strains. In short, this method provides a safe and effective platform for creation of live attenuated RNA viral vaccines.

Classical LAVs were produced experimentally by repeated passaging of a virus in cultured cells, but this method is not always reliable, and safety issues occurred in some cases, for example, when there was a reversion to wild-type virulence. With advances in molecular virology, several novel methods, such as altering replication fidelity (1), deoptimizing codons (2), have been employed in creation of live attenuated vaccines with better-controlled replication and pathogenesis. MicroRNAs (miRNAs) are non-coding endogenous RNAs that direct post-translational regulation of gene expression by interacting with messenger RNAs and targeting them for degradation. miRNA-based gene silencing is also a promising approach to controlling viral replication and may be used to improve the safety of attenuated live vaccine. Recent studies showed many miRNAs are species- and tissue-specific (3-5). These characters of miRNAs can be used to modify the replicative tropism of RNA and DNA viruses (6-9). A number of studies have inserted miRNA target sequence into some viral genomes for successful RNA inhibition (RNAi)(5, 10, 11). Although miRNA targeting is a promising approach to the rational design of LAVs, the risk of accumulating mutations in the miRNA target sequence that cause virulence reversion should be kept in mind.

Previously, design of artificial miRNAs (amiRNAs) that produce functional short interfering RNAs was only limited to DNA viruses and retroviruses (11-14). miRNAs were hypothesized to be problematic in RNA viruses because of the potential degradation of the viral RNA genome during the excision of virus-encoded pre-miRNA. However, a very intriguing study by Varble et al. showed that a miRNA cassette can be successfully inserted into the non-structural (NS) segment of influenza virus (15), and the rescued influenza virus produced functional miRNAs in vitro and in vivo. Results published by Schmid et al showed that replication-incompetent influenza virus could be developed as an RNA viral vector for delivery of amiRNAs (16). Recent published results by other groups also showed that tick-borne encephalitis virus (TBEV), Sindbis virus (SV), and vesicular stomatitis virus (VSV) can produce functional amiRNAs (17-19). These results suggest that it is possible to create live attenuated RNA virus vaccine by incorporating an amiRNA cassette into the RNA virus genome.

The present invention used influenza virus as a test case to design an artificial miRNA insert into a viral gene segment that produces an artificial miRNA (amiRNA) that can be propagated in non-mammalian cells and produced an attenuated live mammalian virus. In one non-limiting example, an miR-93 cassette was used for insertion into NS gene segment of influenza viral genome, which produces an amiRNA specific for an NP gene that would result in a virus that is attenuated in mammalian cells, but could be propagated in chicken eggs at reasonable titers. In animal experiments, vaccination with this novel attenuated influenza virus provides potent and cross immune protection against challenge with lethal influenza viruses.

Results and Discussion. To confirm that a miR-93 backbone would be appropriate for the design, the inventors first analyzed the expression of mature miR-93 in avian cells and mammalian cells by northern blot. The mammalian cells included Madin-Darby canine kidney (MDCK), mouse epithelial fibroblast (MEF), and A549 human lung epithelial cell lines. The DF1 chicken fibroblast cell line served as a representative avian cell line. Upon confirmation of the specificity of miR-93, the inventors designed an artificial miRNA-93NP (amiR-93NP) cassette that would produce an amiRNA targeted against the NP gene of influenza virus. As denoted in bold in FIG. 1A, the sequence within the mature miR-93 loop was replaced with the sequence:

(SEQ ID NO: 1)
5'-AGAUCUUAUAUCUUCGGAGUGUGAUUACCCAACCUCUCCGAAGAAAU

AAGAUCC-3'.

Figure 1B:
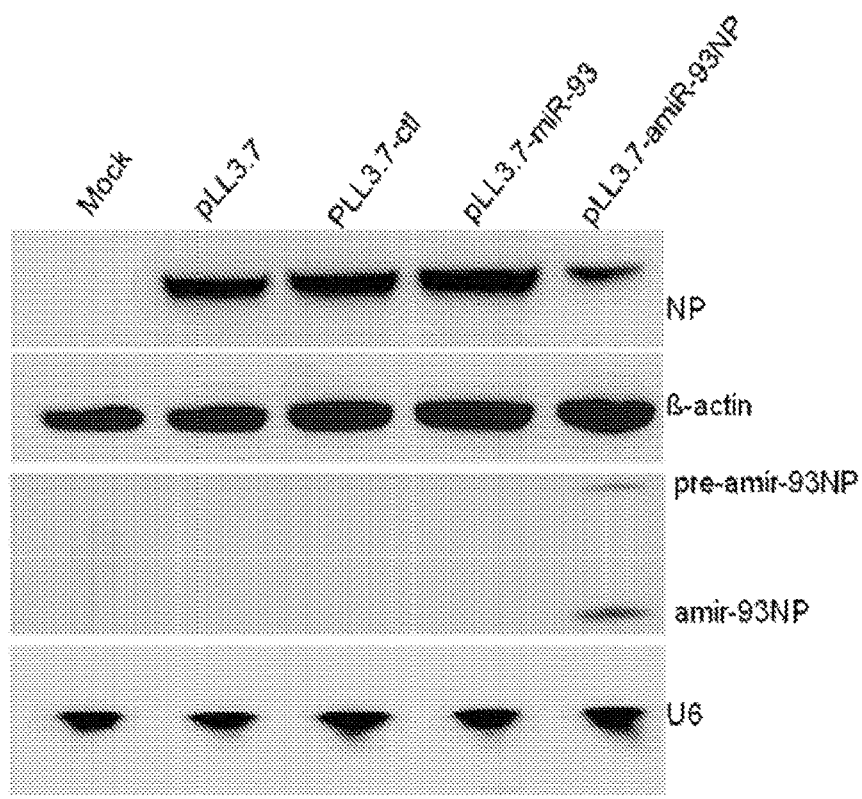
FIG. 1B shows the results from pcDNA-NP with pLL3.7, pLL3.7-ctl, pLL3.7-miR93, or pLL3.7-amiR93NP transfected into 293 T cells, and the cells harvested at 24 h post transfection. Cell lysates were prepared for western blot analysis to detect NP or β-actin proteins, and RNA was prepared for northern blot analyses to detect amiR-93NP expression.
Figure 1C:
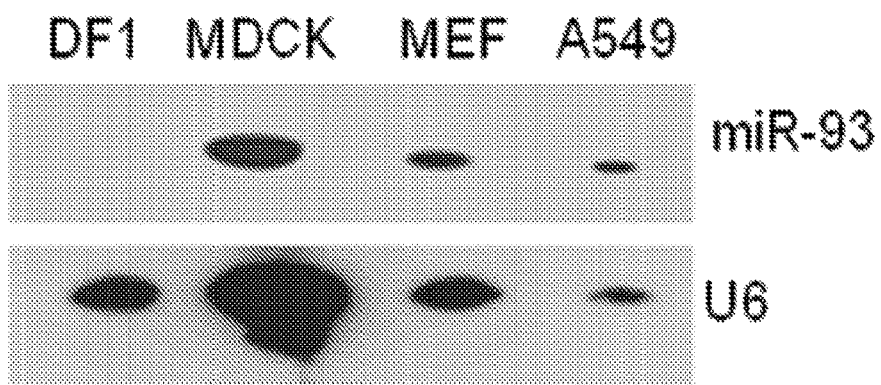
FIGS. 1C and 1D show miR-93 expression profiles in non-infected cells and influenza virus PR8-infected cells.
Figure 1D:
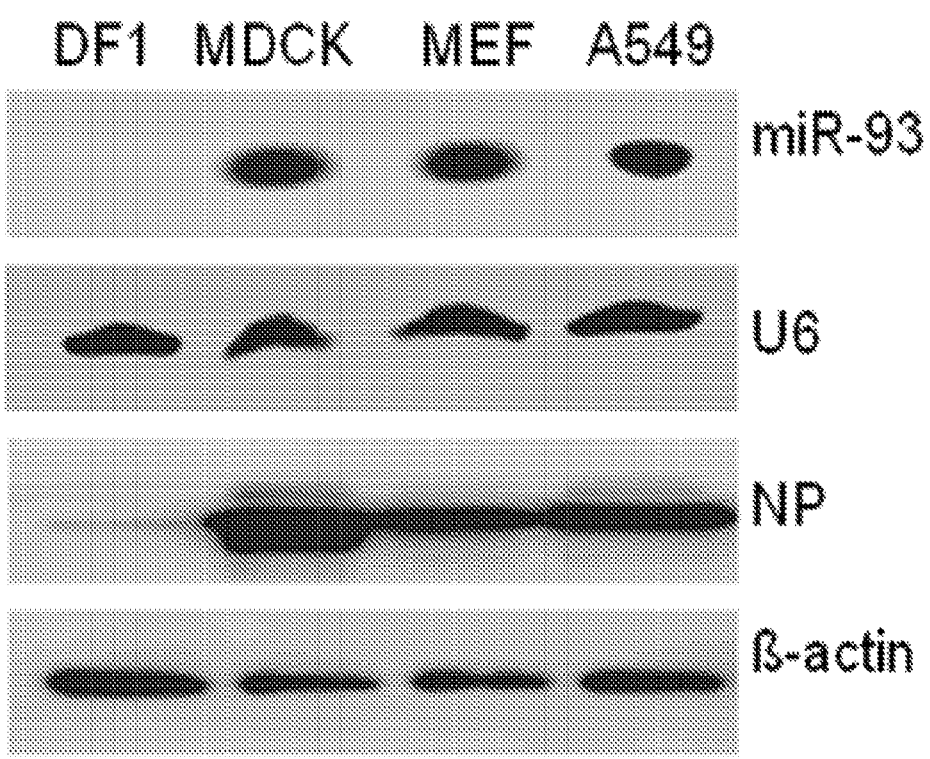

To test whether the NP-targeted amiRNA could be functionally processed, miR-93, amiR-93NP, and a scrambled miRNA control (ctl) of similar size were individually cloned into pLL3.7 plasmids. Each plasmid was co-transfected along with pcDNA-NP into 293T cells. At 24 hours, the expression of NP protein and amiRNA were analyzed by western blot and northern blot, respectively. As shown in FIG. 1B, NP protein expression decreased by about 75% in pLL3.7-amiR-93NP-transfected cells compared with pLL3.7-transfected cells. Furthermore, pre-amiR-93NP and amiR-93NP were detected in cell lysates of pLL3.7-amiR-93NP-transfected cells by northern blot analysis using a probe specific for amiR-93NP. This result indicated that mature and functional amiRNA was produced. The inventors also tested whether miR-93 expression changed after infection with influenza virus. The results showed that miR-93 was not expressed in the uninfected (FIG. 1C) or infected (FIG. 1D) DF1 cells. By contrast, miR-93 was expressed in uninfected and infected MDCK, MEF, and A549 cells (FIGS. 1C and 1D).

Next, the inventors rearranged the NS gene segment of PR8 influenza virus so that NS2 would no longer overlap with the NS1 segment and inserted either the miR-93 or the amiR-93NP cassettes into the newly created intergenic region between NS1 and NS2 (FIG. 2A). Influenza viruses with modified NS gene segments were rescued and propagated in embryonated chicken eggs. Since the influenza virus engineered with amiR-93NP couldn't grow well in MDCK cells, the inventors titrated viruses in chicken eggs, with titers expressed as the 50% egg infective dose ($EID_{50}$).

The modifications in the NS segment resulted in influenza viruses that grew at roughly 10-fold lower titers than the wild-type virus (Table 1).

TABLE 1

Viral growth in chicken eggs ($\times 10^8$ EID$_{50}$)

| Virus | Titer |
|---|---|
| PR8-wt | 5.6 ± 0.56 |
| PR8-ctl | 0.53 ± 0.47 |
| PR8-miR-93 | 0.65 ± 0.31 |
| PR8-amiR-93NP | 0.49 ± 0.61 |

Figure 2D:
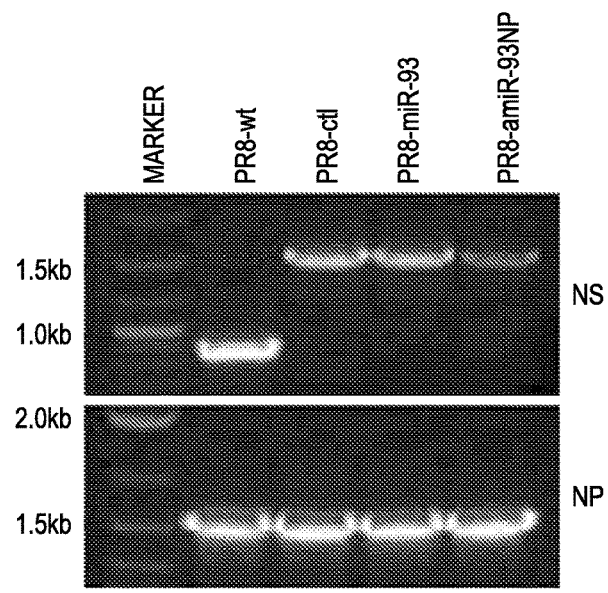

However, there was no significant difference between the titers of viruses engineered with scrambled miRNA, miR-93, or miR-93NP. Next, viruses were concentrated by ultracentrifugation, and the viral genomes were extracted and detected by silver staining. As shown in FIG. 2A, the wild-type NS gene segment migrated at 890 bp, while the modified NS gene segments migrated at 1540 bp, almost overlapping with the NP gene segment (1565 bp). FIG. 2B shows the sequence of the miR-93 locus inserted into the NS gene segment; red denotes the replacement sequence for expression of the artificial microRNA directed against NP. Next, the NS and NP gene segments were amplified by RT-PCR and separated on an agarose gel by electrophoresis. The modified NS gene segments migrated at almost the same size as the NP gene segment (FIGS. 2C and 2D). The NS gene segments were also verified by sequencing. Taken together, these results showed that miRNA/amiRNA insertions into the influenza virus NS gene segment still allowed for successful rescue of influenza viruses from the PR8 DNA plasmid system.

Figure 2E:
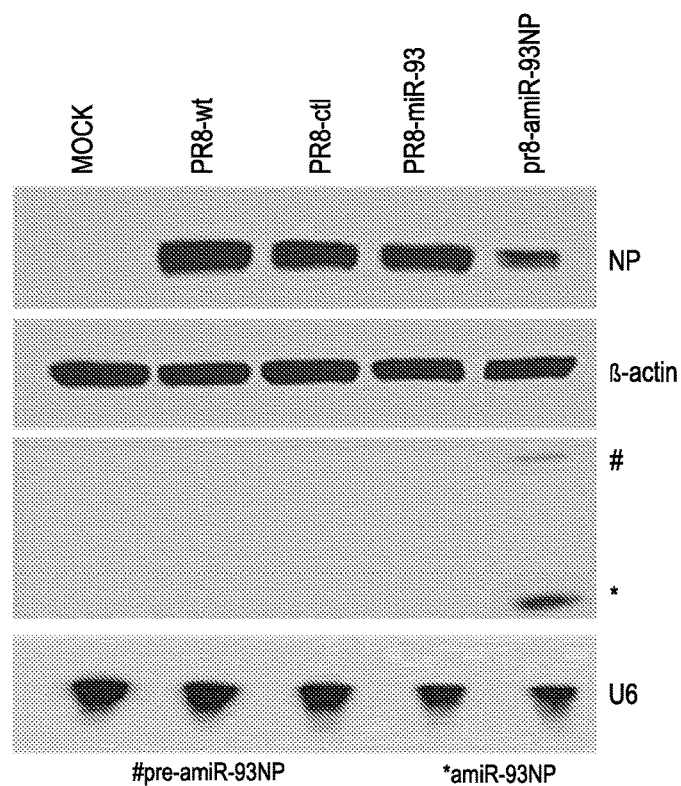
Figure 2F:
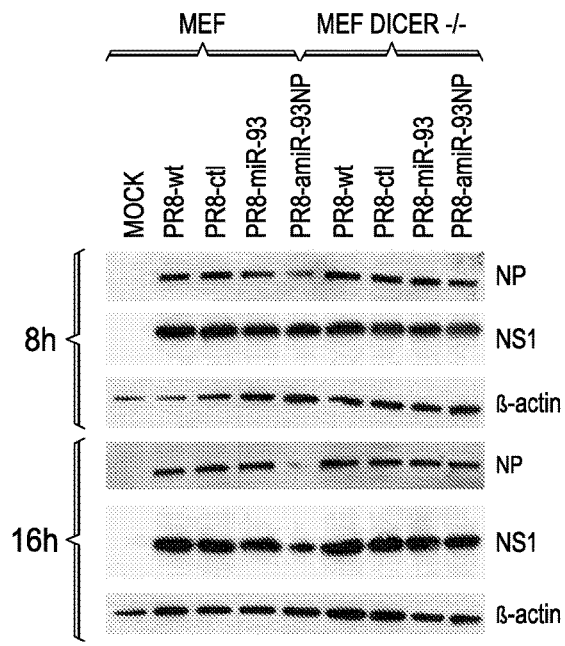

The rescued wild-type and NS-modified PR8 viruses were then evaluated for NP expression and growth characteristics in A549, MEF, MEF Dicer$^{-/-}$, or MDCK cells. Cells were infected with influenza viruses at a multiplicity of infection of 1 EID$_{50}$ (MOI=1). Western blot analysis showed that NP expression was reduced by approximately 40% in A549 cells infected with PR8-amiR-93NP virus compared with A549 cells infected with wild-type PR8 virus at 8 hrs post-infection (FIG. 2E). Expression of pre-amiR-93NP (56 nt) and amiR-93NP (19 nt) was confirmed by northern blot. In MEF wild-type cells infected with PR8-amiR-93NP virus, NP transcripts were reduced by 40% and 87% at 8 and 16 hrs post-infection, respectively, compared with those infected with wild-type virus at the same time points (FIG. 2F).

Figure 3A:
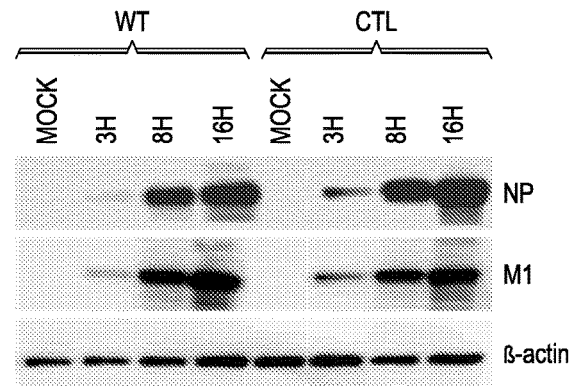
FIGS. 3A and 3B show Replication of PR8-amiR-93NP in the MDCK cell line. MDCK cells were infected with influenza virus and harvested at 8 or 16 hours after infection. NP and M1 proteins were detected by western blot.
Figure 3B:
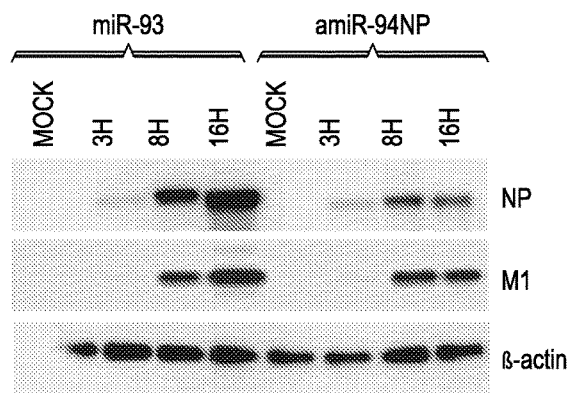

By contrast, NP expression at 8 hrs and 16 hrs post-infection did not differ in MEF Dicer$^{-/-}$ cells infected with PR8-amiR-93NP virus and wild-type PR8 virus. In MDCK cells, infection with PR8-amiR-93NP virus also resulted in reduced expression of NP compared with infection with wild-type virus (FIGS. 3A and 3B). The modified viruses were also attenuated in mice as determined by the 50% mouse lethal dose (MLD$_{50}$). Compared with the wild-type virus, PR8-ctl and PR8-miR-93 virus levels decreased by 20 fold (Table 2). However, the PR8-amiR-93NP virus was substantially more attenuated in mice, and its MLD$_{50}$ was reduced by a factor of $10^4$ compared with the wild-type virus. These results confirmed that the PR8-amiR-93NP virus was substantially attenuated in mammalian species.

TABLE 2

Fifty-percent lethal doses in mouse (EID$_{50}$)

| Virus | MLD$_{50}$ |
|---|---|
| PR8-wt | $10^{1.76}$ |
| PR8-ctl | $10^3$ |
| PR8-miR-93 | $10^{3.17}$ |
| PR8-amiR-93NP | $10^{5.75}$ |

Next, the inventors tested whether the species-attenuated PR8-amiR-93NP virus would stimulate potent immune responses and protection against lethal challenge with wild-type PR8 influenza virus in mice. Mice were intranasally immunized once with different doses of PR8-amiR-93NP, ranging from 1-$10^3$ EID$_{50}$ per mouse, or wild-type PR8 virus at 10 EID$_{50}$ per mouse. First, humoral responses were evaluated by ELISA and micro-neutralization.

Figure 4A:
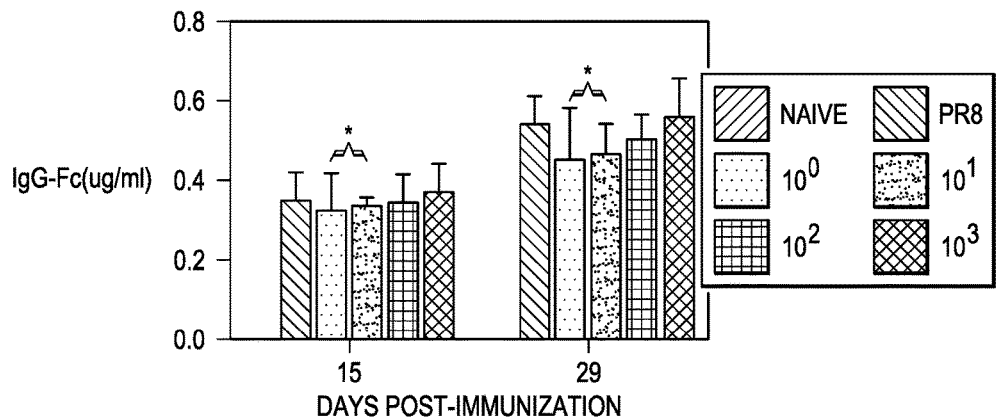
FIGS. 4A to 4C show that humoral immune responses were induced by PR8-amiR-93NP in mice. Mice (n=8) were vaccinated with different doses of PR8-amiR-93NP and bled on days 0, 15, and 29 post-vaccination. HA-specific antibodies IgG Fc (FIG. 4A), IgG1 (FIG. 4B), and IgG2a (FIG. 4C) were measured by ELISA. (*p>0.05, **p<0.05).
Figure 4B:
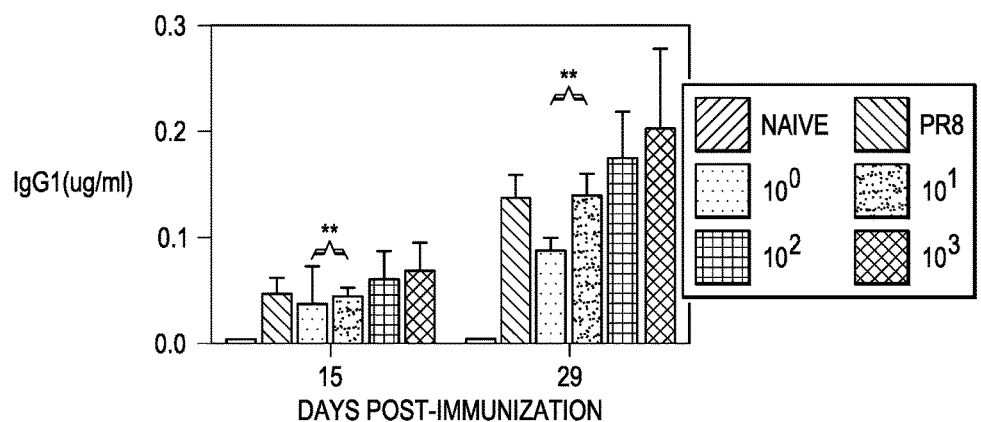
Figure 4C:
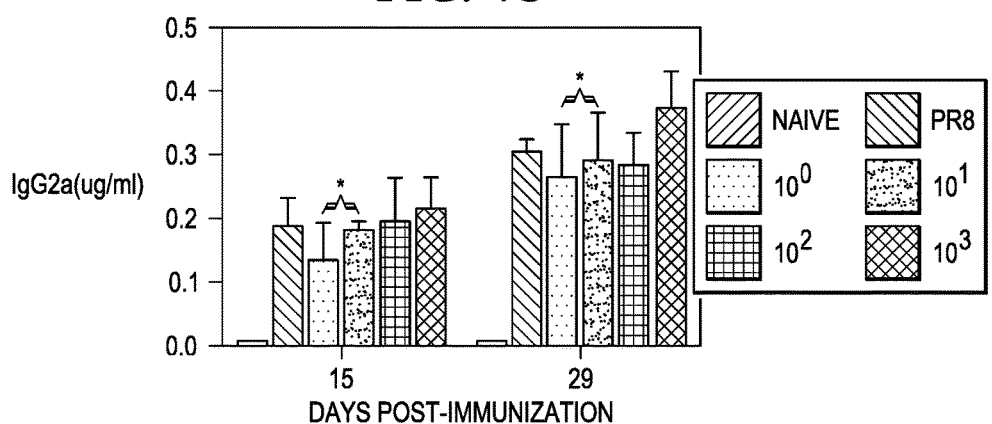
Figure 5A:
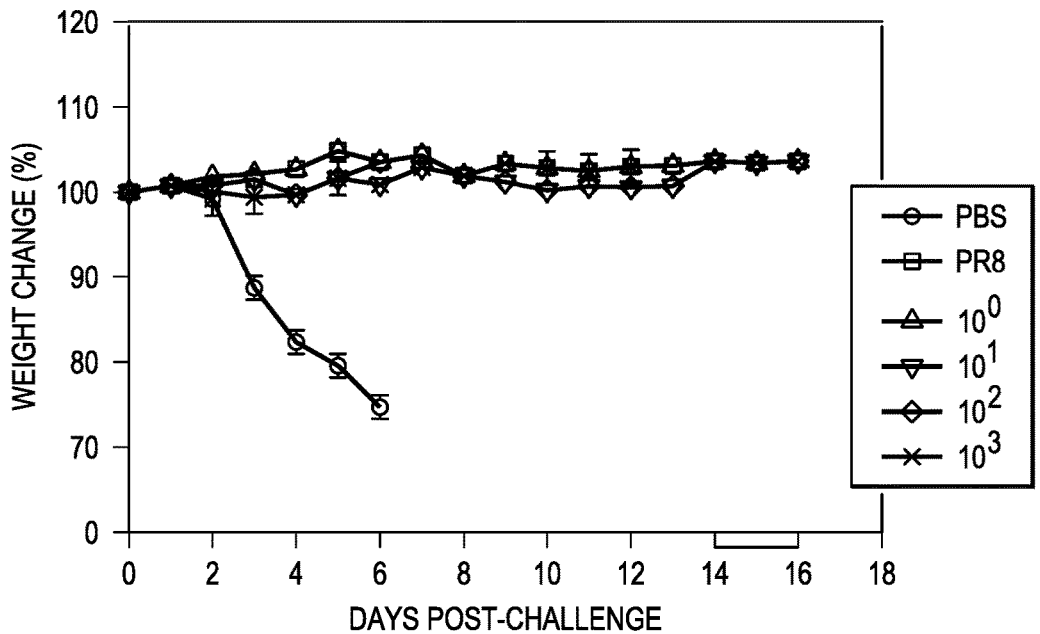
FIGS. 5A to 5F show an evaluation of the protection by PR8-amiR-93NP against lethal challenge with wild-type PR8 influenza virus, pandemic 2009 H1N1 influenza virus or H3N2 influenza virus. Mice (n=8) were vaccinated with different doses of PR8-amiR-93NP and challenged with 100×$LD_{50}$ PR8 influenza virus, $10^4$ PFU HK68 H3N2 influenza virus or 100×$LD_{50}$ CA09 H1N1 pandemic influenza virus.
Figure 5B:
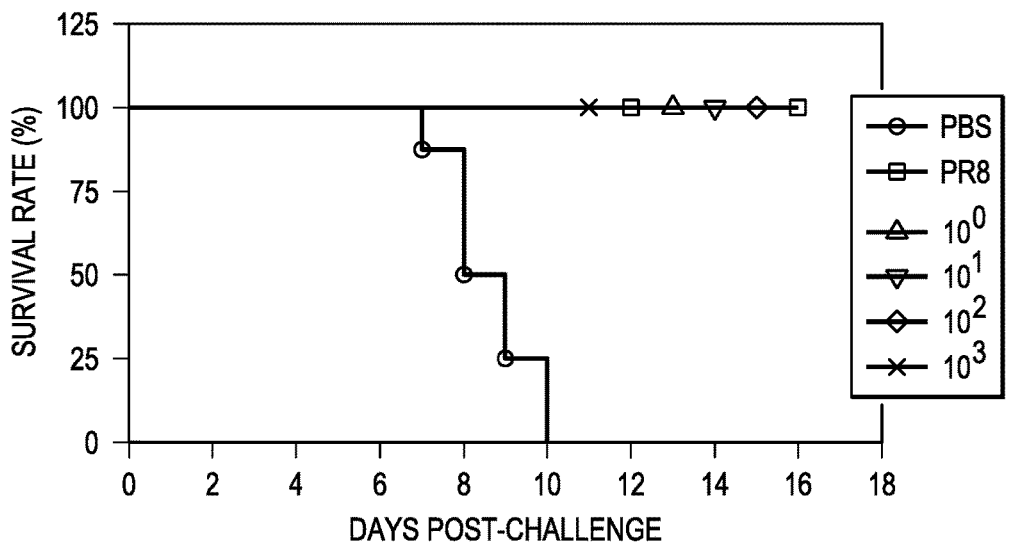

As shown in FIGS. 4A-4C, all doses of PR8-amiR-93NP virus elicited robust total IgG responses that were similar to the response elicited by wild-type PR8 virus on day 15. There was little increase in total IgG levels between days 15 and 29. FIG. 4B shows that by day 15, IgG1 levels became detectable and increased by 3-7 fold by day 29. All groups responded similarly, with the exception that PR8-amiR-93NP vaccinations at $10^0$ and $10^1$ EID$_{50}$ were statistically different on days 15 and 29 (p<0.05). There was no significant difference between IgG and IgG2a levels among immunized groups. In Table 3, results show that immunization with PR8-amiR-93NP induced potent functional IgG neutralizing PR8 wild-type influenza virus. Finally, the challenge results show that immunization with a PR8-amiR-93NP dose as low as 1 EID$_{50}$ was completely protective against lethal challenge with influenza PR8 virus, with no morbidity as measured by weight loss (FIG. 5A) or mortality observed in these mice (FIG. 5B). By contrast, mice that were immunized with PBS exhibited rapid weight loss, and all died by day 10 post-challenge.

TABLE 3

Micro-neutralization titers against PR8 (H1N1) influenza virus in sera from vaccinated mice

| Groups | Titers on day 15 post-immunization | Titers on day 29 post-immunization |
|---|---|---|
| PBS | <10 | <10 |
| PR8 | 1920 ± 684 | ≥2560 |
| $10^0$ EID$_{50}$ | 1282.5 ± 901 | 1460 ± 980 |
| $10^1$ EID$_{50}$ | 1760 ± 889 | ≥2560 |
| $10^2$ EID$_{50}$ | 1920 ± 684 | ≥2560 |
| $10^3$ EID$_{50}$ | 2080 ± 662 | ≥2560 |

Figure 5C:
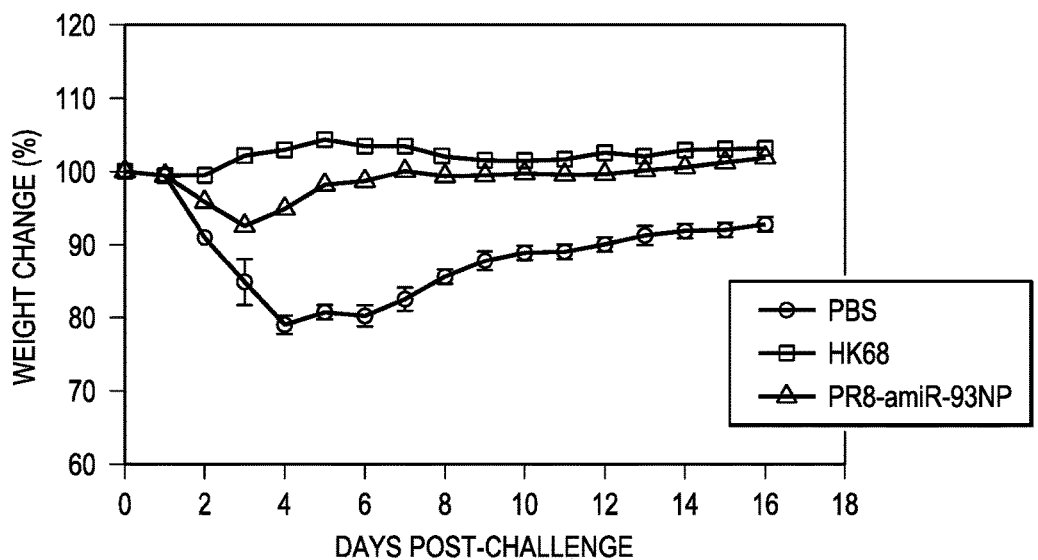
Figure 5D:
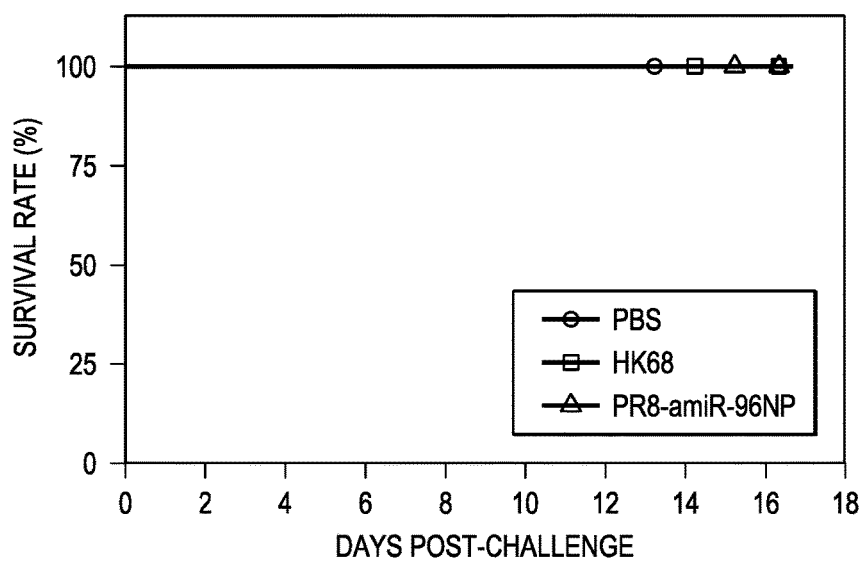
Figure 5E:
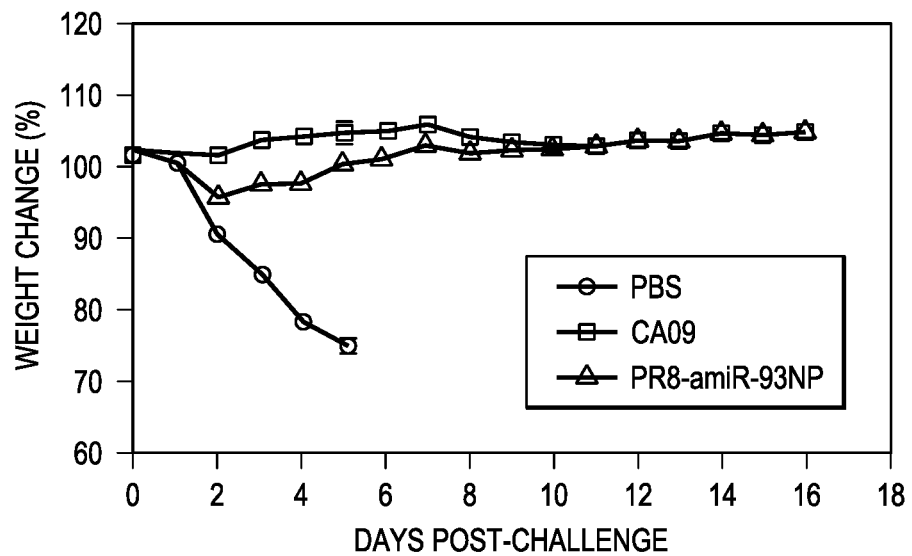
Figure 5F:
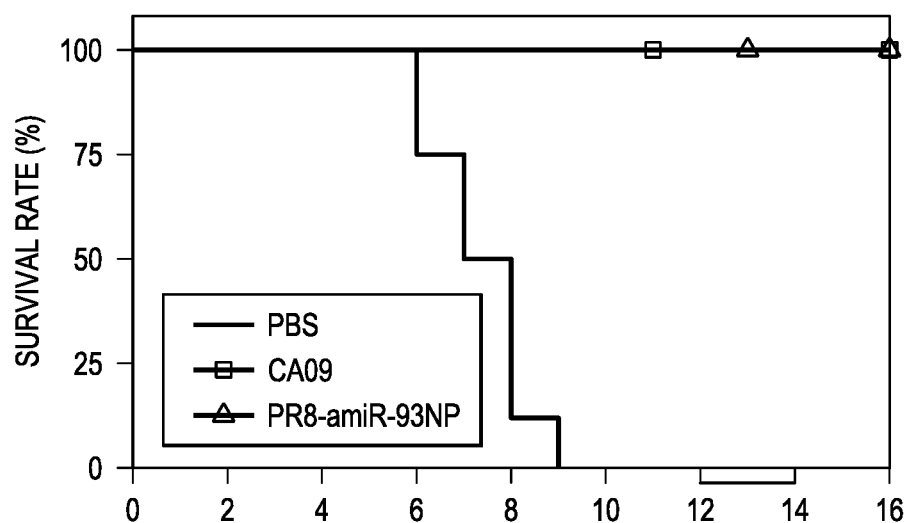

Immunization with PR8-miR-93NP virus also conferred protection against heterologous viral infections. Groups of mice were immunized with $10^2$ EID$_{50}$ of PR8-miR-93NP and challenged at 29 days after immunization. As shown in FIG. 5C, immunization with PR8-miR-93NP or HK68 (H3N2) viruses protected mice against influenza illness caused by challenge with HK68. By contrast, mice administered with PBS lost over 20% of their weight. As this virus is not lethal to mice, all animals survived (FIG. 5D). Immunization with PR8-miR-93NP also conferred protection against lethal challenge with mouse-adapted CA09 (H1N1) pandemic influenza virus. All mice immunized with PR8-miR-93NP or CA09 were protected against morbidity (FIG. 5E) and mortality (FIG. 5F) following lethal challenge with CA09 virus.

Effective delivery is still a challenge for RNAi technology and its successful therapeutic application. It has been recently shown that RNA viruses, including influenza virus, can be modified to produce functional miRNAs (15-17, 19). Engineering influenza virus with naturally occurring or artificial miRNAs (amiRNAs) is appropriate for small RNA delivery. Low pathogenic influenza virus is confined to the respiratory tract and can produce high transient levels of small RNAs, making it an ideal vector for treatment of respiratory infection and diseases. The present invention takes advantage of the species-specific expression pattern of miRNAs to substantially attenuate influenza virus in mammalian species while still allowing for stimulation of an effective immune response.

As shown in this study, the inventors successfully reorganized the NS gene segment of PR8 influenza virus and inserted an amiRNA expression cassette that produced a functional amiRNA. To produce an attenuated influenza vaccine, the inventors selected the NP gene as the target of the amiRNA. So far, chicken eggs are the best known growth vector for influenza virus vaccine seeds. Thus, miR-93, which is not detected in chicken cells, was employed as backbone to produce an amiRNA. While viral titers in viruses with miRNA elements engineered into the NS segment decreased compared with wild-type virus, the inventors were still able to recover viruses at titers of $5 \times 10^7$ $EID_{50}$. Of interest, the PR8-amiR-93NP virus produced NP-specific short hairpin RNA (shRNA) that inhibited NP gene expression. Since the target sequence is highly conserved, prior exposure to the engineered virus dramatically decreases the risk when new influenza virus is introduced.

The inventors demonstrated an effective method by which influenza viruses can be attenuated for safer use as vaccines. The same strategy to make safer vaccine viruses can also be used to express multiple amiRNAs to target various conserved motifs within viral genomes. Specifically, it is possible to simultaneously express a series of amiRNAs targeting different regions of the viral genome in a single amiRNA expression cassette. An engineered PR8-amiR-93NP virus showed pathogenesis in mice when $10^6$ EID viruses were used for challenge. Others have shown that it is feasible to design an miRNA cassette to express multiple amiRNAs in a single vector (20). Thus, to decrease virulence, it is also possible to insert multiple amiRNA expression cassettes into the NS gene segment for use in vaccines. It was found that this method allows for sufficient growth in fertilized chicken eggs and would result in an attenuated virus with little chance of reverting to a fully virulent virus. Furthermore, this method can also be employed to create novel vaccines against other RNA viruses or to attenuate RNA viruses for use as vectors for therapeutic gene delivery.

Eggs and cell culture. Embryonated chicken eggs were purchased from Charles River Laboratories. Upon receipt, the eggs were incubated at 37.5° C. for up to 9 days for use in virus propagation. MDCK cells were cultured in MEM (Sigma) supplemented with 10% FBS, 50 µg/ml gentamicin, and 1 mM sodium pyruvate. HEK293T, MEF, MEF Dicer$^{-/-}$, DF1, and A549 cells were cultured in DMEM (Gibco) supplemented with 10% FBS, 1% penicillin, and 1 µg/ml streptomycin.

Artificial microRNA design and expression. The miR-93 cassette with a scrambled control sequence, the miR-93 locus, and amiR-93NP were synthesized by GenScript and cloned into the microRNA-expressing plasmid pLL3.7 (21). For transfection, $8 \times 10^5$ per well of 293T cells were seeded into 6-well plates. The next day, the cells were transfected with 1 µg plasmid pcDNA-NP with 1 µg pLL3.7, pLL3.7-ctl, pLL3.7-miR-93, or pLL3.7-amir-93NP. At 24 hours after transfection, cells were harvested and lysed. Expression of NP and amiR-93NP were detected by western blot and northern blot, respectively.

Virus design, rescue, and titration. Modified NS gene segments with miR-93 locus and amir-93NP cassette insertions were synthesized by GenScript. Reorganization of the NS gene segment was as described in a previous study (22), relevant portions incorporated herein by reference. The pre-miR93 sequence is provided in FIG. 2 shows the viruses were rescued using a plasmid-based rescue system (23). The viruses designed were wild-type PR8 (PR8-wt), PR8-control (PR8-ctl), PR8-miR-93, and PR8-amiR-93NP. Viral stocks were titrated in chicken eggs and expressed as $EID_{50}$. Briefly, tenfold serial dilutions of viruses were prepared in PBS. Each egg was inoculated with a 100-µl dilution. Virus from allantoic fluid was tested by hemagglutination (HA) assay, and the titer was calculated according to the Reed and Muench method (24).

Mammalian cell infection. Cells were seeded in different culture vessels one day prior to infection. For the infection, cells were washed with Dulbecco's phosphate-buffered saline (DPBS) supplemented with $Ca^{++}/Mg^{++}$ and infected with influenza virus at specified MOIs diluted in fresh medium without serum. After a 1-hour incubation, cells were washed with DPBS again supplemented with $Ca^{++}/Mg^{++}$ before adding culture medium supplemented with 0.3% BSA. Cells were harvested according to assay-dependent requirements. Infection in MDCK cells also required the addition of tosyl phenylalanyl chloromethyl ketone (TPCK)-trypsin to the culture medium.

Northern blot analysis. RNAs were extracted from different cell lines using the miRNeasy Mini Kit (Qiagen) and stored at −80° C. Probes used for northern blot analyses included probes for U6 (5'-CACGAATTTGCGT-GTCATC-CTT-3')(SEQ ID NO:3), miR-93 (5'-CTACCTGCAC-GAACAGCACTTTG-3') (SEQ ID NO:4), and amiR-93NP (5'-GAGGCTTCTTTATTCTAGG-3') (SEQ ID NO:5). Northern blot experiments were performed using the High Sensitive miRNA Northern Blot Assay Kit as per the manufacturer's protocol (Signosis), and membranes were developed with chemiluminescent HRP substrate. Images were acquired using the ImageQuant LAS400 (GE Healthcare).

Western blot analysis. Lysed MDCK cell samples were loaded and separated on 10% SDS-PAGE, then transferred onto nitrocellulose membrane using a semi-dry transblot apparatus (Biorad, cat#1703940). The membrane was blocked in PBS with 1% Tween (PBST) and 5% non-fat milk for 1 hour with an anti-NP monoclonal antibody (Abcam, cat# ab20343) at 4° C. overnight. After washing with PBST, the membrane was incubated with alkaline phosphatase-conjugated goat anti-mouse IgG antibody at room temperature for 1 h. After washing, the membrane was developed with chemiluminescent HRP substrate before imaging.

Virulence test in vivo. Mice (6-8 wk old) were purchased from Jackson Laboratory and divided randomly into groups with four mice in each group. For determination of the $MLD_{50}$, virus was serially diluted in DPBS, and 50 µl were intranasally inoculated into mice anesthetized by injection with ketamine and xylazine. The $MLD_{50}$ was calculated according to the method of Reed and Muench (24). After infection, mice were monitored daily for clinical symptoms, weight loss, and death Animal experimental protocols were approved by the Institutional Animal Care and Use Committee at Texas Tech University Health Sciences Center (IACUC #10020). All animal experiments were carried out in accordance with the US Public Health Service Guide for the Care and Use of Laboratory Animals (NRC Publication, 8th ed.) and other related federal statutes and regulations of the Animal Welfare Act.

Humoral immune response and protective immunity. Mice (6-8 wk old) were randomly divided into groups and intranasally inoculated with 50 µl of diluted influenza virus. Mouse blood was collected on days 15 and 29, and serum was isolated for analysis by micro-neutralization assay and ELISA for anti-HA responses. For testing the IgG antibody concentration in mouse serum, plates were coated with HA of the PR8 virus, and specific IgG, IgG1, and IgG2a were measured in the sera of immunized mice. After the last bleeding, mice were challenged with 100×$LD_{50}$ mouse-adapted PR8 (H1N1), A/California/04/2009(H1N1) (CA09), or $10^4$ PFU A/Hong HK/1/68 (H3N2) (HK68) influenza virus. The challenged mice were monitored for clinical symptoms and survival. ELISA and micro-neutralization were performed as previously described by the inventors (25).

Statistical analysis. Comparisons between vaccinated groups were performed by using a nonparametric one-way ANOVA with the Tukey multiple comparison test and Fisher's exact test. Survival curves were analyzed by log-rank test. The analyses were performed using GraphPad Prism version 5.0 software for Windows (GraphPad Software). P values <0.05 were considered to indicate a significant difference.

It is contemplated that any embodiment discussed in this specification can be implemented with respect to any method, kit, reagent, or composition of the invention, and vice versa. Furthermore, compositions of the invention can be used to achieve methods of the invention.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine experimentation, numerous equivalents to the specific procedures described herein. Such equivalents are considered to be within the scope of this invention and are covered by the claims.

All publications and patent applications mentioned in the specification are indicative of the level of skill of those skilled in the art to which this invention pertains. All publications and patent applications are herein incorporated by reference to the same extent as if each individual publication or patent application was specifically and individually indicated to be incorporated by reference.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. In embodiments of any of the compositions and methods provided herein, "comprising" may be replaced with "consisting essentially of" or "consisting of". As used herein, the phrase "consisting essentially of" requires the specified integer(s) or steps as well as those that do not materially affect the character or function of the claimed invention. As used herein, the term "consisting" is used to indicate the presence of the recited integer (e.g., a feature, an element, a characteristic, a property, a method/process step or a limitation) or group of integers (e.g., feature(s), element(s), characteristic(s), propertie(s), method/process steps or limitation(s)) only.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AB, BBC, AAABCCCC, CBBAAA, CABABB, and so forth. The skilled artisan will understand that typically there is no limit on the number of items or terms in any combination, unless otherwise apparent from the context.

As used herein, words of approximation such as, without limitation, "about", "substantial" or "substantially" refers to a condition that when so modified is understood to not necessarily be absolute or perfect but would be considered close enough to those of ordinary skill in the art to warrant designating the condition as being present. The extent to which the description may vary will depend on how great a change can be instituted and still have one of ordinary skilled in the art recognize the modified feature as still having the required characteristics and capabilities of the unmodified feature. In general, but subject to the preceding discussion, a numerical value herein that is modified by a word of approximation such as "about" may vary from the stated value by at least ±1, 2, 3, 4, 5, 6, 7, 10, 12 or 15%.

Additionally, the section headings herein are provided for consistency with the suggestions under 37 CFR 1.77 or otherwise to provide organizational cues. These headings shall not limit or characterize the invention(s) set out in any claims that may issue from this disclosure. Specifically and by way of example, although the headings refer to a "Field of Invention," such claims should not be limited by the language under this heading to describe the so-called technical field. Further, a description of technology in the "Background of the Invention" section is not to be construed as an admission that technology is prior art to any invention(s) in this disclosure. Neither is the "Summary" to be considered a characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of such claims shall be considered on their own merits in light of this disclosure, but should not be constrained by the headings set forth herein.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

REFERENCES

1. Vignuzzi M, Stone J K, Arnold J J, Cameron C E, & Andino R (2006) Quasispecies diversity determines pathogenesis through cooperative interactions in a viral population. Nature 439(7074):344-348.
2. Yang C, Skiena S, Futcher B, Mueller S, & Wimmer E (2013) Deliberate reduction of hemagglutinin and neuraminidase expression of influenza virus leads to an ultraprotective live vaccine in mice. Proceedings of the National Academy of Sciences of the United States of America 110(23):9481-9486.
3. Zhang R, Wang Y Q, & Su B (2008) Molecular evolution of a primate-specific microRNA family. Molecular biology and evolution 25(7):1493-1502.
4. Berezikov E, et al. (2006) Diversity of microRNAs in human and chimpanzee brain. Nature genetics 38(12):1375-1377.
5. Perez J T, et al. (2009) MicroRNA-mediated species-specific attenuation of influenza A virus. Nature biotechnology 27(6):572-576.
6. Barnes D, Kunitomi M, Vignuzzi M, Saksela K, & Andino R (2008) Harnessing endogenous miRNAs to control virus tissue tropism as a strategy for developing attenuated virus vaccines. Cell host & microbe 4(3):239-248.
7. Edge R E, et al. (2008) A let-7 MicroRNA-sensitive vesicular stomatitis virus demonstrates tumor-specific replication. Molecular therapy: the journal of the American Society of Gene Therapy 16(8):1437-1443.
8. Kelly E J, Hadac E M, Greiner S, & Russell S J (2008) Engineering microRNA responsiveness to decrease virus pathogenicity. Nature medicine 14(11):1278-1283.
9. Lee T C, et al. (2010) Utilizing liver-specific microRNA-122 to modulate replication of dengue virus replicon. Biochemical and biophysical research communications 396(3):596-601.
10. Ylosmaki E, Martikainen M, Hinkkanen A, & Saksela K (2013) Attenuation of Semliki Forest virus neurovirulence by microRNA-mediated detargeting. Journal of virology 87(1):335-344.
11. Kumar M, Follenzi A, Garforth S, & Gupta S (2012) Control of HBV replication by antiviral microRNAs transferred by lentiviral vectors for potential cell and gene therapy approaches. Antiviral therapy 17(3):519-528.
12. Zhang T, et al. (2012) Efficient inhibition of HIV-1 replication by an artificial polycistronic miRNA construct. Virology journal 9:118.
13. Wu Z, Xue Y, Wang B, Du J, & Jin Q (2011) Broad-spectrum antiviral activity of RNA interference against four genotypes of Japanese encephalitis virus based on single microRNA polycistrons. PloS one 6(10): e26304.
14. Boden D, et al. (2004) Enhanced gene silencing of HIV-1 specific siRNA using microRNA designed hairpins. Nucleic acids research 32(3):1154-1158.
15. Varble A, et al. (2010) Engineered RNA viral synthesis of microRNAs. Proceedings of the National Academy of Sciences of the United States of America 107(25):11519-11524.
16. Schmid S, Zony L C, & tenOever B R (2014) A versatile RNA vector for delivery of coding and noncoding RNAs. Journal of virology 88(4):2333-2336.
17. Rouha H, Thurner C, & Mandl C W (2010) Functional microRNA generated from a cytoplasmic RNA virus. Nucleic acids research 38(22):8328-8337.
18. Shapiro J S, Varble A, Pham A M, & Tenoever B R (2010) Noncanonical cytoplasmic processing of viral microRNAs. Rna 16(11):2068-2074.
19. Pica N, Langlois R A, Krammer F, Margine I, & Palese P (2012) NS1-truncated live attenuated virus vaccine provides robust protection to aged mice from viral challenge. Journal of virology 86(19):10293-10301.
20. Chen S C, Stern P, Guo Z, & Chen J (2011) Expression of multiple artificial microRNAs from a chicken miRNA126-based lentiviral vector. PloS one 6(7): e22437.
21. Rubinson D A, et al. (2003) A lentivirus-based system to functionally silence genes in primary mammalian cells, stem cells and transgenic mice by RNA interference. Nature genetics 33(3):401-406.
22. Manicassamy B, et al. (2010) Analysis of in vivo dynamics of influenza virus infection in mice using a GFP reporter virus. Proceedings of the National Academy of Sciences of the United States of America 107(25):11531-11536.
23. Hoffmann E, Neumann G, Kawaoka Y, Hobom G, & Webster R G (2000) A DNA transfection system for generation of influenza A virus from eight plasmids. Proceedings of the National Academy of Sciences of the United States of America 97(11):6108-6113.
24. Reed L H, and H. Muench. (1938) A simple method of estimating fifty percent endpoints. Am. J. Hyg. 27:5.
25. Li J, et al. (2014) Intranasal immunization with influenza antigens conjugated with cholera toxin subunit B stimulates broad spectrum immunity against influenza viruses. Human vaccines & immunotherapeutics 10(6).

What is claimed is:

1. A live attenuated virus comprising:
an isolated virus comprising a viral genome that expresses one or more viral antigens; and
one or more exogenous species-specific artificial microRNAs (amiRNAs), wherein one or more amiRNAs are inserted into the viral genome and expressed thereby, wherein the amiRNAs are ubiquitously expressed in a viral target species cell but not in a viral propagation cell, and wherein the one or more amiRNAs comprise a mature miR-93 loop comprising SEQ ID NO:1, 5'AGAUCUUAUAUCUUCGGAGUGUGAUUAC-CCAACCUCUCCGAAGAAAUAAGAUC-3'.

2. The virus of claim 1, wherein the species-specific microRNA is a mature and functional artificial microRNA that specifically silences influenza Nucleoprotein (NP) gene expression.

3. The virus of claim 1, wherein the microRNA is ubiquitously expressed in mammalian cells but not in avian cells.

4. The virus of claim 1, wherein the microRNA is not expressed in avian cells.

5. The virus of claim 1, wherein the microRNA comprises a miR-93 backbone-based cassette for species-specific microRNA expression.

6. The virus of claim 1, wherein the virus expresses one or more viral antigens that confer protection against H1N1, pandemic H1N1, and H3N2.

7. The virus of claim 1, wherein the virus is packaged into a vaccine.

8. The virus of claim 1, wherein the virus is adapted for pulmonary, oral, nasal, or mucosal administration.

9. The virus of claim 1, wherein the virus is packaged into a vaccine and less than 1,000, 500, 400, 300, 200, 100, 90, 80, 70, 60, 50, 40, 30, 20, 10, or 1 viral particle(s) trigger a humoral and a cellular immune response to the one or more viral antigens.

10. The virus of claim 1, wherein the virus is packaged into a vaccine and less than 1,000, 500, 400, 300, 200, 100, 90, 80, 70, 60, 50, 40, 30, 20, 10 or 1 viral particle(s) confer protective immunity to the virus.

11. The virus of claim 1, wherein the virus has an $EID_{50}$ of 10 or less.

12. The virus of claim 1, wherein the virus comprises multiple artificial miRNA expression cassettes.

13. The virus of claim 1, wherein the virus comprises one or more artificial miRNA expression cassettes in the non-structural (NS) gene segment.

* * * * *

UNITED STATES PATENT AND TRADEMARK OFFICE
CERTIFICATE OF CORRECTION

| | | |
|---|---|---|
| PATENT NO. | : 10,493,146 B2 | |
| APPLICATION NO. | : 15/518781 | |
| DATED | : December 3, 2019 | |
| INVENTOR(S) | : Mingtao Zeng and Junwei Li | |

It is certified that error appears in the above-identified patent and that said Letters Patent is hereby corrected as shown below:

In the Specification

On Column 1, Line 17, before the "FIELD OF THE INVENTION" please insert the following paragraph:
-- STATEMENT OF FEDERALLY FUNDED RESEARCH
This invention was made with U.S. Government support by the NIH/NIAIG grant number R01 AI072139. The government has certain rights in this invention. --

Signed and Sealed this
Twenty-eighth Day of March, 2023

Katherine Kelly Vidal
*Director of the United States Patent and Trademark Office*

SEQUENCE LISTING

<160> NUMBER OF SEQ ID NOS: 6

<210> SEQ ID NO 1
<211> LENGTH: 54
<212> TYPE: RNA
<213> ORGANISM: Artificial Sequence

```
<220> FEATURE:
<223> OTHER INFORMATION: Synthetic primer

<400> SEQUENCE: 1
agaucuuaua ucuucggagu gugauuaccc aaccucuccg aagaaauaag aucc        54

<210> SEQ ID NO 2
<211> LENGTH: 56
<212> TYPE: RNA
<213> ORGANISM: Artificial Sequence
<220> FEATURE:
<223> OTHER INFORMATION: Synthetic primer

<400> SEQUENCE: 2
accuagaaua aagaagccuc ucgaacccau uagugugagg cuucuauauu cuagag      56

<210> SEQ ID NO 3
<211> LENGTH: 22
<212> TYPE: DNA
<213> ORGANISM: Artificial Sequence
<220> FEATURE:
<223> OTHER INFORMATION: Synthetic primer

<400> SEQUENCE: 3
cacgaatttg cgtgtcatcc tt                                          22

<210> SEQ ID NO 4
<211> LENGTH: 23
<212> TYPE: DNA
<213> ORGANISM: Artificial Sequence
<220> FEATURE:
<223> OTHER INFORMATION: Synthetic primer

<400> SEQUENCE: 4
ctacctgcac gaacagcact ttg                                         23

<210> SEQ ID NO 5
<211> LENGTH: 19
<212> TYPE: DNA
<213> ORGANISM: Artificial Sequence
<220> FEATURE:
<223> OTHER INFORMATION: Synthetic primer

<400> SEQUENCE: 5
gaggcttctt tattctagg                                              19

<210> SEQ ID NO 6
<211> LENGTH: 434
<212> TYPE: DNA
<213> ORGANISM: Artificial Sequence
<220> FEATURE:
<223> OTHER INFORMATION: Synthetic primer

<400> SEQUENCE: 6
gtgctaccgc actgtgggta cttgctgctc cagcagggca cgcacagcgt ccgtggaggg    60
aaaggccttt tccccacttc ttaaccttca ctgagagggt ggttgggtc tgtttcactc   120 catgtgtcct agatcctgtg ctacagacct tcctttctgt cctccgtct tggacctcag   180 tcctggggc tccaaagtgc tgttcgtgca ggtagtgtga ttacccaacc ttactgctga   240
gctagcactt cccgagcccc cgggacacgt tctctctgcc aattgtcttc ttggctgagc   300
tccccaagct ccatctgtca tgctggggag cccagtggcg ttcaaaaggg tctggtctcc   360
```

```
ctcacaggac agctgaactc cgggactggc cagtgttgag aggcggagac ttgggcaatt    420
gctggacgct gccc                                                      434
```